(12) United States Patent
Rada

(10) Patent No.: US 6,725,673 B1
(45) Date of Patent: Apr. 27, 2004

(54) APPARATUS AND METHOD FOR PREPARING FROZEN TISSUE SPECIMENS

(76) Inventor: David C. Rada, 248 Lake Shore West, Lake Quivira, KS (US) 66106

( * ) Notice: Subject to any disclaimer, the term of this patent is extended or adjusted under 35 U.S.C. 154(b) by 0 days.

(21) Appl. No.: 10/431,272

(22) Filed: May 7, 2003

(51) Int. Cl.$^7$ .......................... F25D 25/00; B25B 11/00
(52) U.S. Cl. .............................. 62/62; 62/341; 83/915.5
(58) Field of Search ........................... 62/51.1, 62, 320, 62/341, 381, 499; 83/915.5

(56) References Cited

U.S. PATENT DOCUMENTS

| | | | |
|---|---|---|---|
| 3,209,821 A | * 10/1965 | Zeytoonian | ................. 165/185 |
| 3,948,061 A | * 4/1976 | Kidwell | ....................... 62/499 |
| 4,695,339 A | 9/1987 | Rada | |
| 4,752,347 A | 6/1988 | Rada | |
| 5,321,955 A | * 6/1994 | Leonard | ..................... 62/51.1 |
| 5,628,197 A | 5/1997 | Rada | |
| 5,829,256 A | 11/1998 | Rada | |
| 6,094,923 A | 8/2000 | Rada | |
| 6,289,682 B1 | 9/2001 | Rada | |

* cited by examiner

Primary Examiner—Melvin Jones
(74) Attorney, Agent, or Firm—John C. McMahon

(57) ABSTRACT

An apparatus and method for preparing frozen tissue specimens includes a base supporting a pair of rotary motion platforms and a center platform. The rotary motion platforms are each movable from an open, side-by-side position to a closed, center platform-covering position. Each platform includes a series of cryogenic discs equipped with a channel system having a series of radial channels communicating with a peripheral channel for circulation of a cryogenic fluid within the disc structure. The radial channels each include a series of circumferential fins for causing turbulent flow of the cryogen and further increasing heat transfer. The discs have a circumferential seal. The discs may include a radially extending peripheral flange, which serves to reduce disc thickness and thermal mass. The flange may extend selectively to alter the circular shape of the disc. The upper surfaces of the rotating platform discs may have a convex configuration.

14 Claims, 3 Drawing Sheets

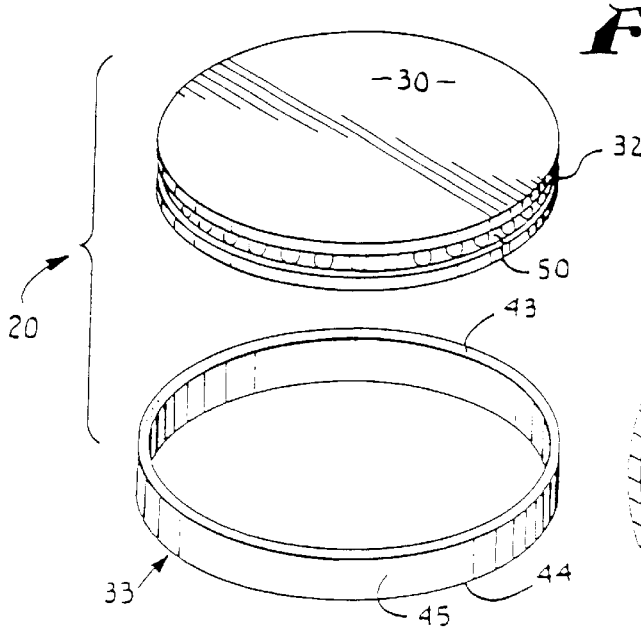
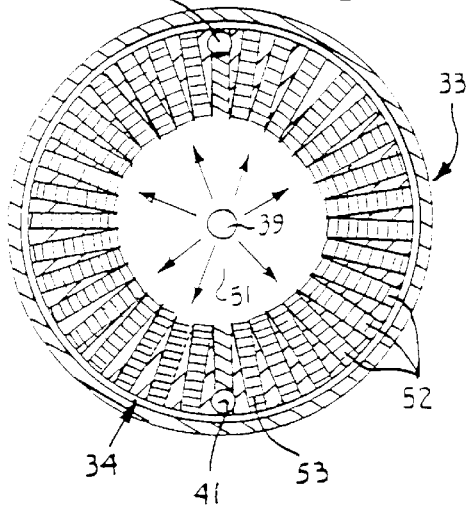
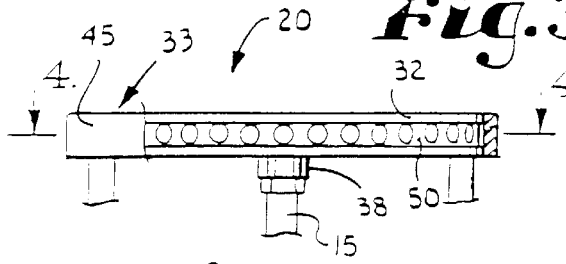
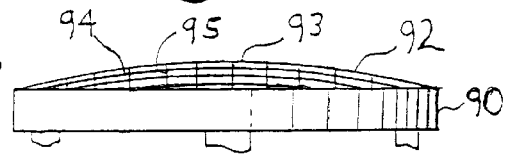
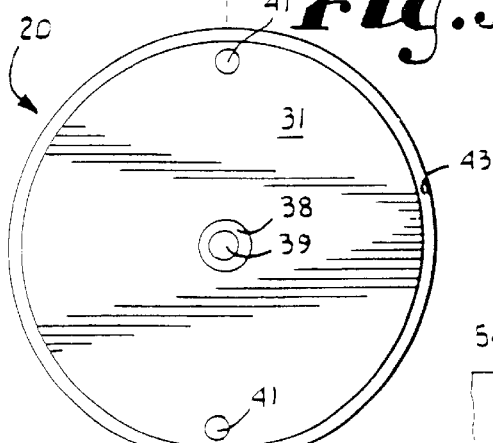
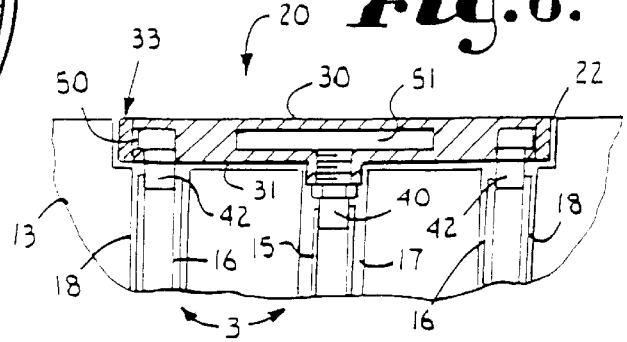

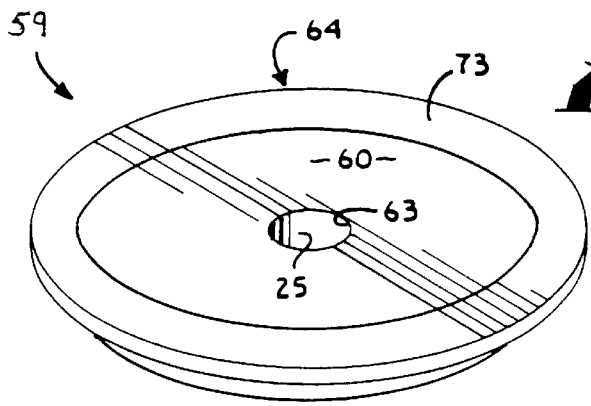
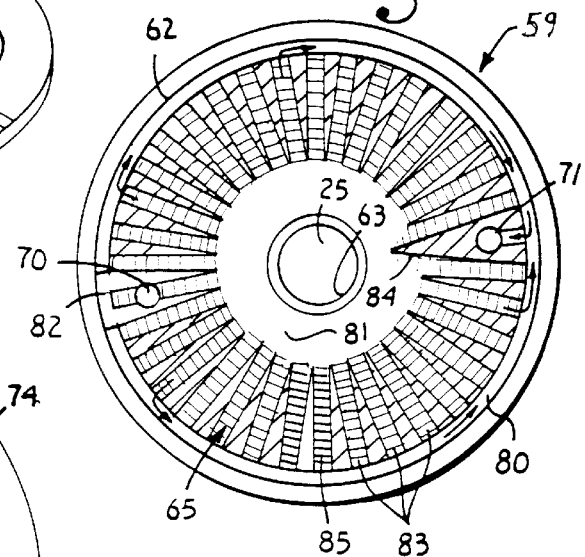
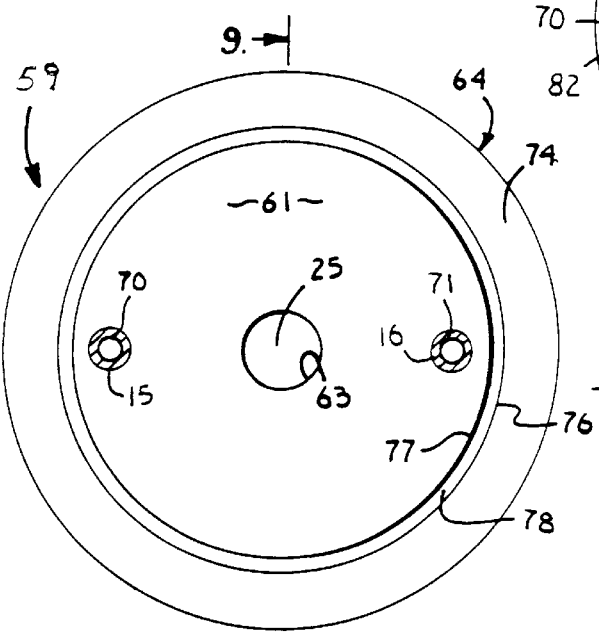
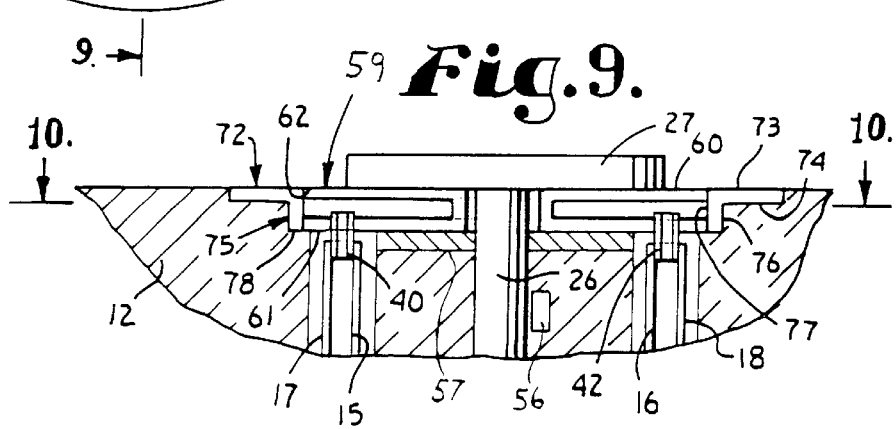

APPARATUS AND METHOD FOR PREPARING FROZEN TISSUE SPECIMENS

BACKGROUND OF THE INVENTION

The present invention is broadly directed to an improved apparatus and method for rapidly freezing tissue specimens at cryogenic temperatures that enhances heat transfer, quickly cools tissue holders and tissue permits use of shaped cryogenic surfaces and facilitates cutting of thin tissue sections. More particularly, it is directed to a tissue freezing apparatus having improved cryogenic structure including a channel system permitting highly effective circulation of a cryogen and transfer of heat thereto so as to rapidly cool tissue specimens.

Biopsy or surgical removal of tissue specimens for histologic examination, is commonly employed for diagnostic purposes. When a lesion is known or suspected to be malignant, the entire mass is generally excised, if possible. An examination technique is often preferably employed in which the entire tumor margin surface area is reviewed under a microscope. This technique involves microscopic screening of the exterior surface area of the tumor for the presence of malignant cells in order to ensure that all such cells have been removed. If practiced effectively, tumor margin surface area examination enhances the likelihood of complete removal of all cells of a localized malignancy.

Once harvested, the tissue sample is preferably quickly frozen at a controlled rate using a cryogenic coolant in order to obtain high quality frozen sections suitable for use in diagnosis. The tissue is then cut into thin layers or sections for histological examination. It is important that the tissue be frozen and the histologic examination performed as quickly as possible, since the patient must be kept waiting pending the microscopic evaluation, in case any additional tissue must be excised. In the past each review of the tissue was comparatively very lengthy, so that a patient had to be maintained in a very uncomfortable state with an open wound for a long period of time. Much of the delay was due to slow freezing of the tissue samples, so fast freezing is very desirable, especially where multiple samples must be taken.

Controlled freezing of the tissue may be accomplished using the methods and devices set forth in Applicant's previous patents, such as U.S. Pat. Nos. 4,695,339; 4,752,347; 5,628,197; 5,829,256; 6,094,923 and 6,289,682, which are incorporated herein by reference. The rate at which specimens can be frozen under such controlled conditions is determined by the rate of heat transfer from a cryogenic fluid, such as liquid nitrogen, to the platform on which the tissue is placed. Specimens must be frozen relatively quickly in order to avoid formation of large water crystals. However, attempts to increase the rate of freezing by use of excessive amounts of cryogenic material may impair control over the freezing process. Specimens that are frozen unevenly or incorrectly may be marred by voids and artifacts that might impair histologic examination and diagnosis. It is also desirable to minimize the quantity of cryogenic fluid that is used, since such fluids are costly and may present certain environmental hazards which must be addressed. Therefore, it is important to enhance heat transfer while maintaining control over specimen freezing conditions and conserving use of cryogenic fluids.

Even a properly prepared tissue specimen that is quickly frozen under controlled conditions may not result in a high quality histologic specimen unless thin tissue sections can be taken easily from the frozen specimen. Compression of the section may occur where difficulty is encountered in cutting thin sections from a frozen specimen. Upon gross examination, compressed tissue sections may appear to be usable for mounting on slides, but will prove to be difficult to evaluate. Badly crumpled sections may be unusable. Compressed and crumpled sections are often produced by the shape of the structure upon which the sections are prepared and frozen.

Accordingly, there is a need for an apparatus and method for evenly and quickly freezing a tissue specimen under controlled conditions while facilitating tissue cutting, conserving cryogenic fluids and providing flexibility in the shape of the cryogenic surface.

SUMMARY OF THE INVENTION

The present invention is directed to improvements that enhance heat transfer in an apparatus and method for preparing frozen tissue specimens. The apparatus includes a base supporting a pair of rotary motion platforms and a center platform. The rotary motion platforms are each movable from an open, side-by-side position to a closed, center platform-covering position. Each platform includes a series of cryogenic discs equipped with a channel system for circulation of a cryogenic fluid within the disc structure. The channel system includes a series of radial channels communicating with a peripheral channel. The radial channels each include a series of interior circumferential fins for causing turbulent flow of the cryogen and further increasing heat transfer. The discs have a circumferential ring seal. The discs for the rotary motion platforms each include a central inlet port and a pair of peripheral outlet ports communicating with the channel system for addition and exhaust of circulated cryogenic fluid. The discs of the center platform include peripheral inlet and outlet ports and a central aperture for receiving a tissue holder. In certain embodiments, the discs include a radially extending peripheral flange, which serves to reduce disc thickness and the mass of the material to be cooled. Such a flange may extend selectively to alter the circular shape of the disc. In some embodiments the upper surfaces of the rotating platform discs have a convex configuration for promoting better tissue samples.

Objects and advantages of this invention will become apparent from the following description wherein are set forth, by way of illustration and example, certain embodiments of this invention.

BRIEF DESCRIIPTION OF THE DRAWINGS

FIG. 2 is an enlarged, exploded view of a first cryodisc for use with the rotary motion platforms and a sealing ring thereof.

FIG. 3 is an enlarged and fragmentary side elevation of the cryodisc shown in FIG. 3, with a portion of the sealing ring broken away to show radial channels thereof.

FIG. 4 is a cross sectional view of the cryodisc of FIG. 2, taken along line 4—4 of FIG. 3 showing the radial channels and a central inlet port thereof.

FIG. 5 is a bottom plan view of a the cryodisc of FIG. 1, showing inlet and outlet ports.

FIG. 6 is a fragmentary cross sectional view, taken along line 6—6 of FIG. 5, showing an internal structure of the cryodisc installed on a rotary motion platform.

FIG. 7 is an enlarged view of a second modified cryodisc for use with a linear motion platform, showing a sealing ring thereof in place.

FIG. 8 is a bottom plan view of the second cryodisc of FIG. 7, showing inlet and outlet ports and a central bore thereof.

FIG. 9 is a fragmentary cross sectional view, taken along line 9—9 of FIG. 8, showing an internal structure of the second cryodisc installed on a linear motion platform, with a tissue holder thereof in place.

FIG. 10 is a cross sectional view, taken along line 10—10 of FIG. 9, showing the linear platform disc with the sealing ring removed and showing radial channels and inlet and outlet ports thereof.

FIG. 11 is a fragmentary side elevational view of a third modified embodiment of a cryodisc in accordance with the invention.

DETAILED DESCRIPTION OF THE INVENTION

Figure 1:
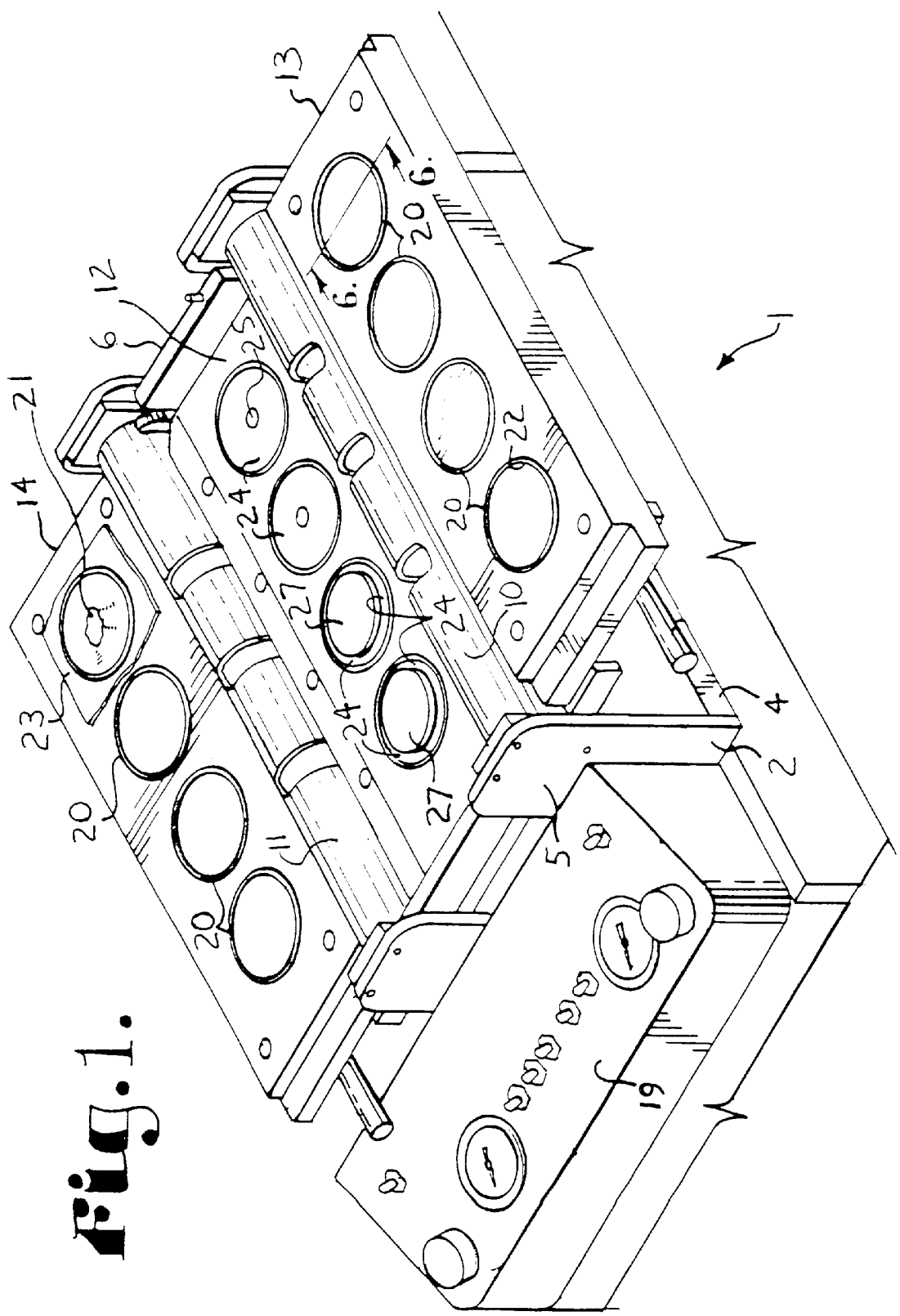
FIG. 1 is a fragmentary perspective view of a tissue freezing apparatus in accordance with the present invention and illustrating the apparatus with both tissue-receiving rotary motion platforms in an open and tissue-receiving configuration and having a plurality of cryodiscs thereon.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

An improved apparatus generally indicated by the reference numeral 1 for preparing frozen tissue specimens in accordance with the present invention is depicted in FIG. 1 and includes a platform mechanism 2 and a fluid transfer system 3. The platform mechanism 2 includes a base 4 supporting fixed, upstanding front and rear support panels 5 and 6. The panels 5 and 6 support between them a pair of laterally spaced, generally horizontal columns 10 and 11 in vertically spaced relation to the base 4. A central linear motion platform 12 is located between the support panels 5 and 6 and is supported on the base 4 by well known structure permitting the platform 12 to be raised and lowered in spaced relation to the base 4. Each support column 10 and 11 is coupled with a respective rotary motion platform 13 or 14 in laterally spaced relation to the central platform 12 and in vertically spaced relation to the base 4. The columns 10 and 11 are pivotally coupled with the support panels 5 and 6, permitting selective axial rotation of a column 10 or 11 and its respective rotary motion platform 13 or 14 from an open position, in which the platform 13 or 14 is laterally adjacent to the central platform 12, to a covering position, in which the platform 13 or 14 is vertically adjacent the central platform 12.

In addition to the respective rotary motion platforms 13 and 14, the columns 10 and 11 also support associated components of the fluid transfer system 3, best shown in FIGS. 6 and 9. The fluid transfer system 3 includes a flexible cryogen supply conduit 15, which in turn is coupled with a source (not shown) of a liquid cryogenic material, such as liquid nitrogen, and a return conduit 16. The rotary motion platforms 13 and 14 and linear motion platform 12 each include a series of bores 17 and 18, for receiving the respective supply and return conduits 15 and 16. A control panel 19 is mounted on the front of the apparatus 1 for use by an operator in control and use of the apparatus 1.

Each of the rotary motion platforms 13 and 14 includes a series of four spaced cryodiscs 20 (designated "rotary" cryodiscs, for clarity) for receiving tissue specimens 21. Each rotary cryodisc 20 is encircled by a groove 22 that is in fluidic communication with a vacuum pump (not shown). A plastic sheet 23 is supplied for placement over a specimen 21 in covering relationship to the groove 22 and a vacuum is drawn through the groove 22. The vacuum serves to draw the sheet 23 tightly against the specimen 21, the cryodisc 20 and the surface of the rotary motion platform 13 or 14. In this manner, the sheet 23 compresses the specimen 21 against the cryodisc 20 and air pockets between the specimen 21 and the cryodisc 20 are drawn radially outward and removed by the vacuum.

The linear motion platform 12 has four somewhat similar cryodiscs 24 (designated "linear" cryodiscs for clarity), each having a central hollow bore 25 sized for receiving the stem 26 of a tissue-receiving plate 27, best shown in FIG. 9.

The rotary platform cryodiscs 20 depicted in FIGS. 2–6 each include a top or upper surface 30, a bottom or lower surface 31 with a sidewall 32 extending therebetween and an annular circumferential sealing ring or seal 33. Each cryodisc 20 is equipped with a channel system 34 for circulation throughout the cryodisc 20 of a cryogenic fluid delivered via the fluid transfer system 3. The illustrated cryodisc top surface 30 is generally planar and smooth, for receiving a tissue specimen 21. It is also foreseen that the top surface may be tapered peripherally and circumferentially from its center or the surface may be convex. Such a curved construction yields a frozen specimen 21 having slightly elevated edges, which serves to compensate for any curling of the tissue margins that may occur during freezing and reduce the number of hard to work with and damaged specimens.

The rotary cryodisc top surface 30 is preferably coated with a polymeric composition, especially a tetrafluoroethylene, such as is sold under the trademark Teflon® by Du Pont, to facilitate quick release of the specimen 21 (FIG. 1). The bottom surface 31 is also generally planar and smooth and includes a central stem 38 that is apertured to provide an inlet port 39 for coupling with the supply conduit 15 through a nipple 40. The bottom surface 31 also includes a pair of circumferentially spaced apertures or outlet ports 41, for coupling with the return conduit 16 by means of nipples 42. The sealing ring 33 also includes a top or upper surface 43 and a bottom or lower surface 44 with a sidewall 45 therebetween.

The top and bottom surfaces 30 and 31 of the cryodisc 20 are depicted in FIGS. 2 and 5 to be generally circular in shape and identical in diameter, and the sealing ring 33 is sized to encircle the disc sidewall 32 in snug or generally sealing relationship, with the sealing ring top and bottom surfaces 43 and 44 and aligned so as to be contiguous with and extend generally planar with respect to the disc top and bottom surfaces 30 and 31 respectively.

As best shown in FIGS. 3, 4 and 6, the channel system 34 has a circular manifold configuration for circulation of a cryogenic fluid throughout the cryodisc 20. The channel system 34 includes a circumferential groove or perimeter channel 50 in the cryodisc sidewall 32 and an axial reservoir area or collection chamber 51 which is concentric with the inlet port 39. A series of spaced radial, but centrally converging, bores or channels 52 communicate between the circumferential channel 50 and reservoir 51. The radial channels 52 are each equipped with a series of spaced and radially inward projecting fins, ridges or serrations 53 for operably increasing turbulence in the cryogenic fluid and enhancing heat transfer from the cryodisc 20 to the cryogenic fluid.

During usage of the apparatus 1, tissue specimens 21 are first placed on the cryodisc 20 as noted before. The cryodisc 24 are cooled to cryogenic temperatures at the same time as the cryodisc 20. The plate 27 with attached stem are first moistened with isopropyl alcohol on the underside thereof and then the stems 26 are placed in respective bores 25 with the plate 27 somewhat spaced from the surface of a respective cryodisc 24 until the platform 13 or 14 is rotated and a respective cryodisc 20 with specimen 21 thereon engages a respective plate 27 at which time the engaged plate 27 drops and comes in touching contact with the outer surface of the cryodisc 24. In this manner, the plate 27 becomes a near room temperature object holder engaging the cold specimen 21 which warms near the engagement and then is again quickly recooled when the plate 27 engages the cryodisc 24. This improves adhesion between the specimen 21 and plate 27, while the alcohol cooperator with frost on the coating of the surface of the cryodisc 24 to enhance heat transfer and provide rapid and consistent cooling to the plate 27.

FIGS. 7 to 10 show an apparatus that is similar in most ways to the apparatus shown in FIGS. 1 to 6 except for a different cryodisc described below and that there is a thermostat 56 and a heater element 57 that are used to warm the cryodiscs to a desired temperature after usage, so as to ready for the next usage.

Modified linear platform cryodiscs 59 are shown in FIGS. 7–10 that are of similar construction to the cryodiscs 24, each including a top or upper surface 60, a bottom or lower surface 61, a circumferential outer sidewall 62 extending therebetween and an axial inner sidewall 63 therebetween. The inner sidewall 63 forms a central bore 25, sized for receiving the stem 26 of a tissue receiving plate 27. A circumferential sealing ring or seal 64 is configured for mated sealing engagement with the outer sidewall 62. Each linear cryodisc 59 is equipped with a channel system 65 similar to that of the rotary cryodiscs 20 and used for circulation of the same cryogenic material delivered via the fluid transfer system 3.

The cryodisc top surface 60 is generally planar and smooth, for supporting the tissue receiving plate 27 and providing maximum thermal contact for heat transfer between the plate 27 and the cryodisc 59. The bottom surface 61 is also generally planar and smooth and includes peripherally spaced inlet and outlet ports 70 and 71 for coupling with the respective supply and return conduits 15 and 16 via nipples 40 and 42. As shown in FIG. 9, the sealing ring 64 is generally L-shaped when viewed in cross-section including a radially outward extending upper flange portion 72 having upper and lower surfaces 73 and 74, and a lower, disc-circumscribing portion 75 having an outer sidewall or skirt portion 76, an inner sidewall 77, and a lower or bottom surface 78 therebetween.

The top and bottom surfaces 60 and 61 of the linear cryodisc 59 are generally circular in shape and identical in diameter, and the sealing ring 64 is sized to encircle the disc outer sidewall 62 in substantially sealing relationship with the sealing ring flange upper surface 73 aligned to form a contiguous surface with the disc top surface 60 and the sealing ring lower portion bottom surface 78 aligned to form a contiguous surface with the disc bottom surface 61.

This construction permits the top surface 60 of the cryodisc 59 to extend radially outwardly beyond the lower portion 75. In this manner, the mass of the cryodisc 59 to be cooled is reduced in proportion to the size of the usable surface, thus minimizing the quantity of cryogenic fluid necessary to lower the temperature the cryodisc 59 and specimen. While the flange 72 and lower portion 75 are depicted herein as being of unitary construction, it is foreseen that the flange portion 72 may be of unitary construction with the top surface 60 of the linear disc 59, with the lower portion 75 serving as a sealing ring 72. It is also foreseen that shape of the top surface 60 including the flange portion 72 when viewed from above may be altered to a non-circular configuration, such as for example, triangular or other multilateral, ellipsoid or eccentric shape.

The channel system 65 depicted in FIG. 10 includes a perimeter groove or channel 80 in the cryodisc outer sidewall 62 and an axial reservoir area or collection chamber 81 which concentrically surrounds the inner sidewall 63 forming the bore 25. The channel 80 is generally circumferential, but is interrupted by a channel flow-directing stop 82 which extends along the sidewall 62 for a short distance adjacent the inlet port 70. A series of outwardly spaced but centrally converging radial bores or channels 83 communicate between the channel 80 and reservoir 81, except in the area of the outlet port 71, where a flow-directing dam 84 is provided to block the flow of cryogenic fluid directly from the reservoir 81 to the outlet port 71. The radial channels 83 are each equipped with a series of spaced fins, ridges or serrations 85 for producing turbulence and enhancing heat transfer.

The cryodiscs 20 and 24 are both preferably constructed of a material having a high coefficient of heat transfer, such as a metal, with aluminum being particularly preferred. The circumferential sealing rings 33 and 64 are preferably constructed of a heat-shrink aluminum alloy to ensure a tight seal between the discs 20 and 24 and their respective rings 33 and 64. Those skilled in the art will appreciate that any other suitable thermally conductive material may also be employed. The channel systems 34 and 65 are preferably constructed by drilling a series of evenly outwardly spaced radial channels 52 and 83 inwardly from the sidewall 32 or outer sidewall 62, although it is foreseen that they may also be of cast or molded construction. The fins 53 and 85 are formed by threading or tapping the respective channels 52 and 83 or by other suitable means. Because the linear cryodisc 59 includes a central bore 25 for receiving the tissue holder 27, the drill making the bores 83 is preferably equipped with a limit or stop to avoid breaching the inner sidewall 63. The channel adjacent the outlet port 71 is not bored through to the central reservoir, leaving the flow-directing dam 84. The channels are then tapped and a groove is cut into the sidewall 32 and outer sidewall 62, except for the area of the flow directing stop 82.

While the outstanding flanges 72 of the sealing rings 64 for use with the linear platform cryodiscs 59 advantageously reduce the thermal mass of the cryodiscs 59 to be cooled, it is foreseen that the rings 64 may be constructed without the flanges 72, with a structure similar to the sealing rings 33 for use with the rotary cryodiscs 20. It is also foreseen that the sealing rings 33 for use with the rotary cryodiscs 59 may be constructed to include flange structure similar to the flanges 72.

In use, supply and return conduits 15 and 16 of the fluid transfer system 3 are installed into respective bores 17 and 18 of the rotary motion platforms 13 and 14 and the linear motion platform 12. The supply and return conduits 15 and 16 are coupled with respective nipples 40 and 42, which in turn are coupled with inlet and outlet ports 39 and 41 and 70 and 71 of respective cryodiscs 20 and 59. The cryodiscs 20 and 59 are then installed so that the lower surfaces 31 and 61 engage structure of the respective rotary and linear motion platforms.13 and 14 and 12. A quantity of liquid nitrogen or other cryogenic fluid is conveyed via the supply conduit 15 from a storage vessel to the inlet ports 39 and 70 of the cryodiscs 20 and 59.

In the case of the rotary motion cryodiscs 20, the supply conduit 15 conveys the liquid nitrogen through the inlet port 39 and into the axial reservoir 51. The nitrogen flows outwardly from the reservoir 51, into the radial channels 52, where it passes over the fins 53. The fins 53 cause turbidity in the flow, which enhances heat transfer from the structure of the cryodisc 20 to the liquid nitrogen. Nitrogen gas flows into the perimeter channel 50, which is sealed by the sealing ring 33 to prevent its escape to atmosphere. The nitrogen gas travels around the perimeter channel 50 until it reaches the outlet ports 41, where it is conveyed away via return conduits 16.

A portion of the supply conduit 15 also conveys a quantity of liquid nitrogen from the reservoir to the inlet port 70 of one or more linear platform cryodiscs 59. The fluid travels through an associated radial channel 83, passing over the fins 85 to the central reservoir 81, where it flows along the inner surface of the inner sidewall 63, which surrounds the central bore 25. A portion of the liquid encounters the flow-directing dam 84, which prevents the liquid from exiting directly from the outlet port 71. The liquid circulates from the central reservoir 81 through the radial channels 83 until it reaches the perimeter channel 80. The liquid is prevented by the flow-directing stop 82 from by passing and exiting via the inlet port 70. As the liquid nitrogen warms and gasifies, nitrogen gas passes outwardly from the perimeter channel 80 through the outlet port 71 and is conveyed away via the return conduits 16.

In a method of use, the undersurfaces of a plurality of tissue receiving plates 27 are moistened with 70% isopropyl alcohol as noted previously and the plates 27 are held in a conventional covered moistening tray until use. When a tissue plate 27 is placed onto a frosted linear cryodisc 59, the linear motion platform 12 elevates and contact is made between the lower surface of the plate 27 and the upper surface of the frosted cryodisc 60. Advantageously, consistent and extremely rapid heat transfer occurs between the tissue plate 27 and the cryodisc 59.

A quantity of cryogenic fluid is circulated throughout the fluid transfer system 3 in the rotary and linear cryodiscs 20 and 59, as previously described. Circulation of the liquid chills the rotary discs 20 to a preferred temperature of about −30° C. to about −40° C. in about 45 seconds and the linear discs 24 of the prior embodiment in about 60 seconds. Where the cryodiscs 59 are equipped with flanges 72, the chilling time is reduced to about 30 seconds. One or more tissue specimens 21 are placed on rotary cryodiscs 20 and each is covered by a plastic sheet 23. The vacuum system (not shown) is actuated to flatten the sheets 23 against the tissue specimens 21, removing any air bubbles. Once a tissue specimen 21 is frozen, the associated rotary motion platform 13 or 14 containing the frozen specimens 21 is rotated from its lateral, or side-by-side position with respect to the linear motion platform 12 to a vertically covering relationship wherein the frozen specimens 21 are brought into contacting relationship with the tissue receiving plates 27 for transfer of the specimens 21 to the plates 27.

Shown in FIG. 11 is a third modified cryodisc 90. The cryodisc 90 is similar to the cryodisc 20 described above except as noted. The cryodisc 90 has an upper surface 92 that is convex with, being highest at a center 93 of the cryodisc 90. The cryodisc surface 92 is covered with a non stick coating 94 that has a crosshatched pattern 95 thereon. The cryodisc 90 is used similar to the cryodisc 20 except that the specimen 21 is urged to follow the contour of the surface 92, when place thereon.

It is to be understood that while certain forms of the present invention have been illustrated and described herein, it is not to be limited to the specific forms or arrangement of parts described and shown.

What is claimed and desired to be secured by Letters Patent is as follows:

1. In an apparatus for quick freezing a tissue specimen, wherein a first platform member rotates about an axis relative to a second platform member and having a cryogenic system in operable fluidic connection with the first and second platform members, the improvement comprising:
    a) each of said platform members having a first and a second cylindrically shaped cryodisc thereon respectively for chilling by a cryogenic fluid; said first cryodisc being in a covering relationship to said second cryodisc when said first platform is rotated over said second platform;
    b) said cryodiscs each including a channel system having an inlet and an outlet in fluidic connection with said cryogenic system for circulation of a cryogenic fluid and exhaust of a gas;
    c) said channel system including an internal chamber, a peripheral channel and a plurality of radial channels communicating therebetween; and
    d) at least some of said radial channels including a plurality of fins for causing turbulent flow of said cryogenic fluid and increasing heat transfer from said cryodisc to said cryogenic fluid.

2. The apparatus as set forth in claim 1, further including:
    a) a peripheral sealing member coupled with each of said cryodiscs in sealing relationship with respective peripheral channels.

3. The apparatus as set forth in claim 1, wherein said cryodiscs associated with said first platform member include:
    a) an upper freezing surface;
    b) a lower platform-contacting surface; and
    c) said freezing surface tapers radially downwardly toward said lower surface.

4. The apparatus as set forth in claim 1, wherein:
    a) said cryodiscs associated with said first platform member include an upper freezing surface and a lower platform-contacting surface with a sealing member therebetween; and
    b) said freezing surface extends radially outward beyond said lower surface for providing an enlarged specimen freezing surface area of reduced thickness compared to a remainder of said cryodisc.

5. The apparatus as set forth in claim 4, wherein:
    a) portions of said freezing surface extend selectively outward beyond said lower surface for providing an enlarged specimen freezing surface area having a non-circular shape.

6. The apparatus as set forth in claim 1, wherein said cryodiscs associated with said first platform member include:
    a) an upper surface and a lower surface, said peripheral channel located therebetween;
    b) a radially outward sealing member coupled with said cryodisc in sealing relationship with said peripheral channel;
    c) said channel system inlet being centrally and axially located relative to said lower surface; and d) said channel system outlet being peripherally located on said lower surface in spaced relation to said inlet.

7. The apparatus as set forth in claim 6, wherein:
   a) said channel system inlet is in fluidic communication with said internal chamber; and
   b) said channel system outlet is in fluidic communication with said peripheral channel.

8. The apparatus as set forth in claim 1, wherein said cryodiscs associated with said second platform member include:
   a) an upper surface and a lower surface, said peripheral channel located therebetween and radially outward facing;
   b) a central aperture having a sidewall extending between said upper and lower surfaces;
   c) a sealing member coupled with said cryodisc and overlapping in sealing relationship relative to said peripheral channel;
   d) said channel system inlet is located near a periphery of said lower surface; and
   e) said channel system outlet is located near the periphery of said lower surface in spaced relation to said inlet.

9. The apparatus as set forth in claim 8, wherein:
   a) said peripheral channel includes a flow-directing stop adjacent said inlet for directing a flow of cryogenic fluid from said inlet away from said peripheral channel and into said internal chamber; and
   b) said radial channel adjacent said outlet includes a flow directing dam for directing a flow of cryogenic fluid from said internal chamber away from said outlet and into said peripheral channel.

10. A cryogenic freezing platform for quick freezing a tissue specimen, and comprising:
    a) a cylindrically shaped cryodisc, having a surface for receiving a tissue specimen for freezing;
    b) said cryodisc including a channel system having an inlet and an outlet in fluidic connection with a cryogenic system for circulation of a cryogenic fluid and exhaust of a gas;
    c) said channel system including an internal chamber, a peripheral channel and a plurality of radial channels communicating therebetween; and
    d) each of said radial channels including a plurality of fins for causing turbulent flow of said cryogenic fluid and increasing heat transfer from said cryodisc to said cryogenic fluid.

11. The apparatus as set forth in claim 10, including:
    a) means directing a flow of a cryogenic fluid from said inlet into one of said radial channels to said internal chamber; and
    b) means directing said flow of a cryogenic fluid from said internal chamber through one of said radial channels to said peripheral channel for passage to said outlet.

12. The apparatus as set forth in claim 10, including:
    a) passage structure directing a flow of a cryogenic fluid from said inlet into said peripheral channel for passage to said outlet.

13. In a cryogenic tissue freezing apparatus having at least one cryodisc for receiving and quickly cooling a tissue specimen; the improvement comprising:
    a) said cryodisc having a plurality of radially extending channels adapted to direct flow of cryogenic through the cryodisc; and
    b) at least some of the channels include a plurality of fins adapted to produce turbulence in said cryogenic fluid and increase heat transfer from said cryodisc to said cryogenic fluid.

14. In a method of quick freezing a tissue specimen by cooling said sample on a cryogenic disc and then transferring the specimen to an upper surface of an object holder; the improvement including the steps of:
    a) prior to transferring said specimen to said object holder, coating an undersurface of said object holder with alcohol; and
    b) subsequent to transferring said specimen to said object holder, engaging said object holder under surface with a chilled structure to quickly cool said object holder.

* * * * *